US009028553B2

(12) United States Patent
Lindenmann et al.

(10) Patent No.: US 9,028,553 B2
(45) Date of Patent: May 12, 2015

(54) SELF-PIVOTING SPINAL IMPLANT AND ASSOCIATED INSTRUMENTATION

(75) Inventors: Philippe Lindenmann, Basel (CH); Sean Saidha, Basel (CH); Cyril Baudouin, Riedisheim (FR); Peter Fatone, Exton, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 713 days.

(21) Appl. No.: 12/612,886

(22) Filed: Nov. 5, 2009

(65) Prior Publication Data

US 2011/0106259 A1    May 5, 2011

(51) Int. Cl.
*A61F 2/44* (2006.01)
*A61F 2/46* (2006.01)
(Continued)

(52) U.S. Cl.
CPC .............. *A61F 2/4465* (2013.01); *A61F 2/4611* (2013.01); *A61F 2/4684* (2013.01); *A61F 2002/2835* (2013.01); *A61F 2002/3008* (2013.01); *A61F 2002/30378* (2013.01); *A61F 2002/30383* (2013.01); *A61F 2002/30538* (2013.01); *A61F 2002/30594* (2013.01); *A61F 2002/30604* (2013.01); *A61F 2002/30616* (2013.01); *A61F 2002/30772* (2013.01); *A61F 2002/3082* (2013.01); *A61F 2002/30841* (2013.01); *A61F 2002/30843* (2013.01); *A61F 2002/30879* (2013.01); *A61F 2002/30892* (2013.01); *A61F 2002/4475* (2013.01);
(Continued)

(58) Field of Classification Search
USPC ......... 623/17.11, 17.16; 606/99; 81/419, 420, 81/424.5, 426, 451, 452; 403/112
See application file for complete search history.

(56) References Cited

U.S. PATENT DOCUMENTS 4,927,425 A    5/1990 Lozier
4,941,481 A * 7/1990 Wagenknecht ................. 606/59
(Continued)

FOREIGN PATENT DOCUMENTS

CA    2534357    9/2012
DE    10241948    4/2004
(Continued)

OTHER PUBLICATIONS

Synthes Spine,"Vertebral Spacer-PR. Vertebral body replacement device intended for use in the thoracolumbar spine" (Brochure), 2002, US.
(Continued)

*Primary Examiner* — Christian Sevilla
(74) *Attorney, Agent, or Firm* — Baker & Hostetler LLP

(57) ABSTRACT

An intervertebral implant includes an insertion end, an opposing engagement end, and first and second opposed main surfaces configured to contact respective adjacent vertebral endplates. Each of the first and second main surfaces has an anterior edge, a posterior edge, and extends between the insertion and engagement ends. Anterior and posterior walls are formed between the first and second main surfaces and along the respective anterior and posterior edges and converge at the insertion and engagement ends. A slot is formed at the engagement end and extends continuously between and at least partially along the anterior and posterior walls. A post is positioned within the slot, spaced from at least one of the anterior and posterior walls and extending at least partially between the first and second main surfaces. The post includes a plurality of exposed facets and is configured for engagement with a pivotable insertion instrument.

18 Claims, 13 Drawing Sheets

(51) Int. Cl.
*A61F 2/28* (2006.01)
*A61F 2/30* (2006.01)

(52) U.S. Cl.
CPC . *A61F2002/4622* (2013.01); *A61F 2002/4627* (2013.01); *A61F 2002/4628* (2013.01); *A61F 2310/00017* (2013.01); *A61F 2310/00023* (2013.01)

(56) References Cited

U.S. PATENT DOCUMENTS

| | | | |
|---|---|---|---|
| 5,171,240 A | 12/1992 | Hanwong | |
| 5,190,549 A | 3/1993 | Miller et al. | |
| 5,476,466 A | 12/1995 | Barrette et al. | |
| 5,658,336 A | 8/1997 | Pisharodi | |
| 5,702,463 A | 12/1997 | Pothier et al. | |
| 5,707,371 A | 1/1998 | Metz-Stavenhagen | |
| 5,772,661 A | 6/1998 | Michelson | |
| 5,782,830 A | 7/1998 | Farris | |
| 5,860,973 A | 1/1999 | Michelson | |
| 5,893,890 A | 4/1999 | Pisharodi | |
| 6,174,311 B1 | 1/2001 | Branch | |
| 6,245,108 B1 | 6/2001 | Biscup | |
| 6,309,421 B1 | 10/2001 | Pisharodi | |
| 6,319,257 B1 | 11/2001 | Carignan et al. | |
| 6,425,920 B1 | 7/2002 | Hamada | |
| 6,428,544 B1 | 8/2002 | Ralph et al. | |
| 6,447,544 B1 | 9/2002 | Michelson | |
| 6,579,318 B2 | 6/2003 | Varga et al. | |
| 6,599,294 B2 | 7/2003 | Fuss et al. | |
| 6,648,915 B2 | 11/2003 | Sazy | |
| 6,676,703 B2 | 1/2004 | Biscup | |
| 6,699,288 B2 | 3/2004 | Moret | |
| 6,764,491 B2 | 7/2004 | Frey et al. | |
| 6,767,366 B2 | 7/2004 | Lee et al. | |
| 6,830,570 B1 | 12/2004 | Frey et al. | |
| 6,852,127 B2 | 2/2005 | Varga et al. | |
| 6,974,480 B2 | 12/2005 | Messerli et al. | |
| 7,060,073 B2 | 6/2006 | Frey et al. | |
| 7,060,096 B1 | 6/2006 | Schapf et al. | |
| 7,115,132 B2 | 10/2006 | Errico et al. | |
| 7,169,182 B1 | 1/2007 | Errico et al. | |
| 7,192,447 B2 | 3/2007 | Rhoda | |
| 7,235,081 B2 | 6/2007 | Errico et al. | |
| 7,235,082 B2 | 6/2007 | Bartish et al. | |
| 7,320,688 B2 | 1/2008 | Foley et al. | |
| 7,361,193 B2 | 4/2008 | Frey et al. | |
| 7,404,795 B2 | 7/2008 | Ralph et al. | |
| 7,470,273 B2 | 12/2008 | Dougherty-Shah | |
| 7,473,268 B2 | 1/2009 | Zucherman et al. | |
| 7,575,580 B2 | 8/2009 | Lim et al. | |
| 7,608,080 B2 | 10/2009 | Shipp et al. | |
| 7,806,932 B2 | 10/2010 | Webb et al. | |
| 7,811,292 B2 | 10/2010 | Lo et al. | |
| 7,901,458 B2 | 3/2011 | Deridder et al. | |
| 7,935,148 B2 | 5/2011 | Edie et al. | |
| 7,959,675 B2 | 6/2011 | Gately | |
| 7,988,695 B2 | 8/2011 | Dye | |
| 7,988,699 B2 | 8/2011 | Martz et al. | |
| 8,043,293 B2 | 10/2011 | Warnick | |
| 2002/0065560 A1 | 5/2002 | Varga et al. | |
| 2004/0019356 A1* | 1/2004 | Fraser et al. | 606/102 |
| 2004/0059420 A1* | 3/2004 | Michelson | 623/17.16 |
| 2004/0153065 A1 | 8/2004 | Lim | |
| 2004/0186574 A1 | 9/2004 | Varga et al. | |
| 2005/0038431 A1 | 2/2005 | Bartish et al. | |
| 2005/0096745 A1 | 5/2005 | Andre et al. | |
| 2006/0106460 A1 | 5/2006 | Messerli et al. | |
| 2006/0116767 A1 | 6/2006 | Magerl et al. | |
| 2006/0229627 A1 | 10/2006 | Hunt et al. | |
| 2007/0010886 A1* | 1/2007 | Banick et al. | 623/17.11 |
| 2007/0142843 A1 | 6/2007 | Dye et al. | |
| 2007/0162138 A1* | 7/2007 | Heinz | 623/17.16 |
| 2007/0208343 A1 | 9/2007 | Magerl et al. | |
| 2007/0213737 A1 | 9/2007 | Schermerhorn et al. | |
| 2007/0225726 A1 | 9/2007 | Dye et al. | |
| 2007/0282441 A1 | 12/2007 | Stream et al. | |
| 2008/0009880 A1* | 1/2008 | Warnick et al. | 606/99 |
| 2008/0015701 A1* | 1/2008 | Garcia et al. | 623/17.16 |
| 2008/0051890 A1 | 2/2008 | Waugh et al. | |
| 2008/0065082 A1 | 3/2008 | Chang et al. | |
| 2008/0077150 A1 | 3/2008 | Nguyen | |
| 2008/0077241 A1 | 3/2008 | Nguyen | |
| 2008/0077247 A1 | 3/2008 | Murillo et al. | |
| 2008/0119935 A1 | 5/2008 | Alvarez | |
| 2008/0140085 A1 | 6/2008 | Gately et al. | |
| 2008/0306488 A1 | 12/2008 | Altarac et al. | |
| 2009/0234364 A1* | 9/2009 | Crook | 606/99 |
| 2009/0276049 A1 | 11/2009 | Weiland | |

FOREIGN PATENT DOCUMENTS

| | | |
|---|---|---|
| EP | 346129 A1 | 12/1989 |
| EP | 0557686 | 9/1993 |
| EP | 356112 B1 | 12/1993 |
| EP | 637439 A1 | 2/1995 |
| EP | 425542 B1 | 3/1995 |
| EP | 734702 A1 | 10/1996 |
| EP | 419564 B1 | 8/1998 |
| EP | 855886 A1 | 8/1998 |
| EP | 1093760 A2 | 4/2001 |
| EP | 720455 B1 | 1/2002 |
| EP | 712607 B1 | 2/2002 |
| EP | 615428 B1 | 3/2002 |
| EP | 752830 B1 | 6/2002 |
| EP | 1222898 A3 | 8/2002 |
| EP | 1265562 A2 | 12/2002 |
| EP | 916323 B1 | 1/2003 |
| EP | 1290985 A2 | 3/2003 |
| EP | 1294321 A1 | 3/2003 |
| EP | 836455 B1 | 4/2003 |
| EP | 812167 B1 | 5/2003 |
| EP | 703757 B1 | 8/2003 |
| EP | 855887 B1 | 8/2003 |
| EP | 1221914 B1 | 9/2003 |
| EP | 1219248 A3 | 1/2004 |
| EP | 1219268 A3 | 1/2004 |
| EP | 1344509 A3 | 2/2004 |
| EP | 1391188 A1 | 2/2004 |
| EP | 831759 B1 | 3/2004 |
| EP | 1092395 B1 | 4/2004 |
| EP | 1129668 B1 | 5/2004 |
| EP | 901351 B1 | 8/2004 |
| EP | 836457 B1 | 9/2004 |
| EP | 732093 B1 | 11/2004 |
| EP | 814718 B1 | 11/2004 |
| EP | 1197181 B1 | 11/2004 |
| EP | 1124510 B1 | 12/2004 |
| EP | 1488755 A1 | 12/2004 |
| EP | 1508307 A1 | 2/2005 |
| EP | 988003 B1 | 5/2005 |
| EP | 1346695 B1 | 12/2005 |
| EP | 1221915 B1 | 2/2006 |
| EP | 1389983 B1 | 8/2006 |
| EP | 1684675 A1 | 8/2006 |
| EP | 1009338 B1 | 10/2006 |
| EP | 1709920 A3 | 10/2006 |
| EP | 1722722 A1 | 11/2006 |
| EP | 1374806 B1 | 12/2006 |
| EP | 1525863 A3 | 1/2007 |
| EP | 1764066 A1 | 3/2007 |
| EP | 840580 B1 | 4/2007 |
| EP | 1009337 B1 | 6/2007 |
| EP | 1514519 A3 | 7/2007 |
| EP | 1618848 B1 | 7/2007 |
| EP | 1442732 B1 | 9/2007 |
| EP | 1153574 B1 | 2/2008 |
| EP | 1302182 B1 | 8/2008 |
| EP | 1437105 B1 | 10/2008 |
| EP | 1905931 B1 | 12/2008 |
| EP | 2016924 A3 | 4/2009 |
| EP | 2058014 A1 | 5/2009 |
| EP | 1829503 B1 | 9/2009 |
| EP | 1383449 B1 | 11/2009 |

(56) References Cited

FOREIGN PATENT DOCUMENTS

| | | |
|---|---|---|
| EP | 1 905 391 | 1/2010 |
| EP | 1439773 B1 | 1/2010 |
| EP | 1437988 B1 | 3/2010 |
| EP | 1500372 B1 | 3/2010 |
| EP | 1596764 B1 | 3/2010 |
| EP | 1841385 | 3/2010 |
| EP | 1549259 B1 | 4/2010 |
| EP | 1762202 B1 | 1/2011 |
| EP | 1400221 B1 | 9/2011 |
| EP | 1833428 B1 | 4/2012 |
| EP | 1653892 B1 | 4/2013 |
| FR | 2703580 A1 | 10/1994 |
| FR | 2736537 | 1/1997 |
| FR | 2738475 | 3/1997 |
| FR | 2817463 | 6/2002 |
| FR | 2841125 | 12/2003 |
| WO | WO97/14377 A1 | 4/1997 |
| WO | WO01/68005 A2 | 9/2001 |
| WO | WO01/95838 A1 | 12/2001 |
| WO | 0217823 A1 | 3/2002 |
| WO | WO02/17823 A1 | 3/2002 |
| WO | WO 04/000176 | 12/2003 |
| WO | WO 04/000177 | 12/2003 |
| WO | WO 2004/069033 | 8/2004 |
| WO | WO 2005/011539 | 2/2005 |
| WO | WO 2005/041825 | 5/2005 |
| WO | WO2005/041825 A1 | 5/2005 |
| WO | WO2005/087143 | 9/2005 |
| WO | WO 2006/079356 | 8/2006 |
| WO | WO 2007/016801 | 2/2007 |
| WO | WO 2007/070751 | 6/2007 |
| WO | WO 2007/093900 | 8/2007 |
| WO | WO 2008/036636 | 3/2008 |
| WO | WO2008/079953 A3 | 10/2008 |
| WO | WO 2011/056172 | 5/2011 |

OTHER PUBLICATIONS

Synthes Spine, "T-PLIF Spacer Instruments, Technique Guide" (Brochure), 2001, US.
Synthes Spine, "Vertebral Spacer-PR" (Brochure), 2002, US.
Synthes Spine, "OPAL Spaper System. Oblique posterior atraumatic lumbar spacer system, Technique Guide" (Brochure), 2008, US.
Supplementary EP Search Report for European Application 03813779 dated Nov. 4, 2010, 4 pages.
Supplementary EP Search Report for European Application 03786692 dated Sep. 19, 2008, 2 pages.
Supplementary EP Search Report for European Application 03749686 dated Feb. 3, 2011, 3 pages.
Supplementary EP Search Report for European Application 03752374 dated Mar. 20, 2007, 4 pages.
Supplementary EP Search Report for European Application 01908625 dated Dec. 15, 2006, 4 pages.
Supplementary EP Search Report for European Application 00980805 dated Feb. 26, 2007, 3 pages.

* cited by examiner

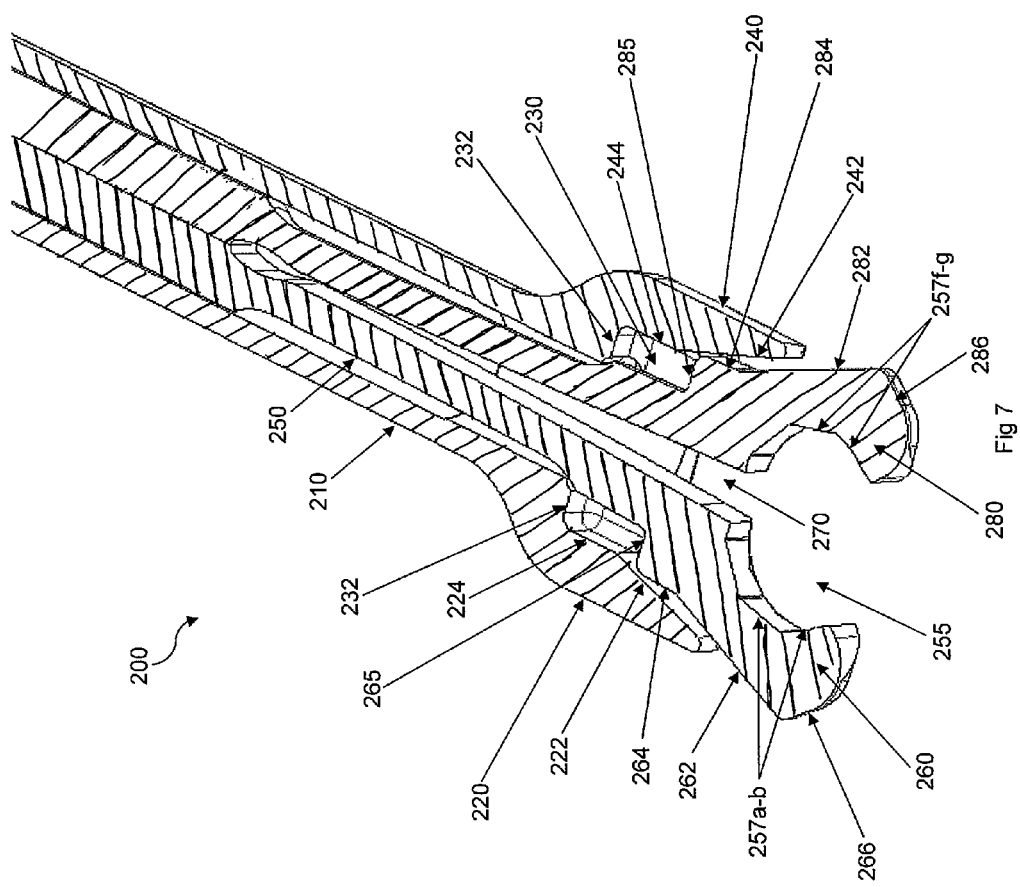

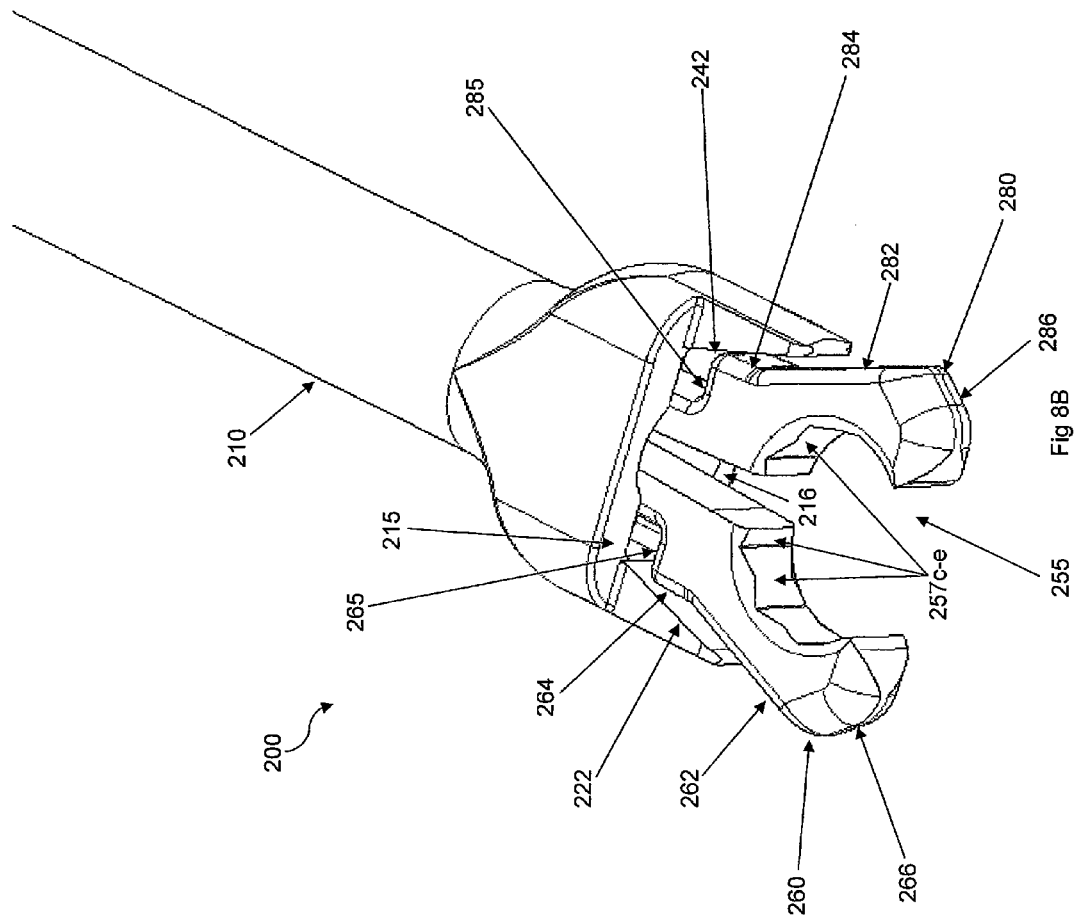

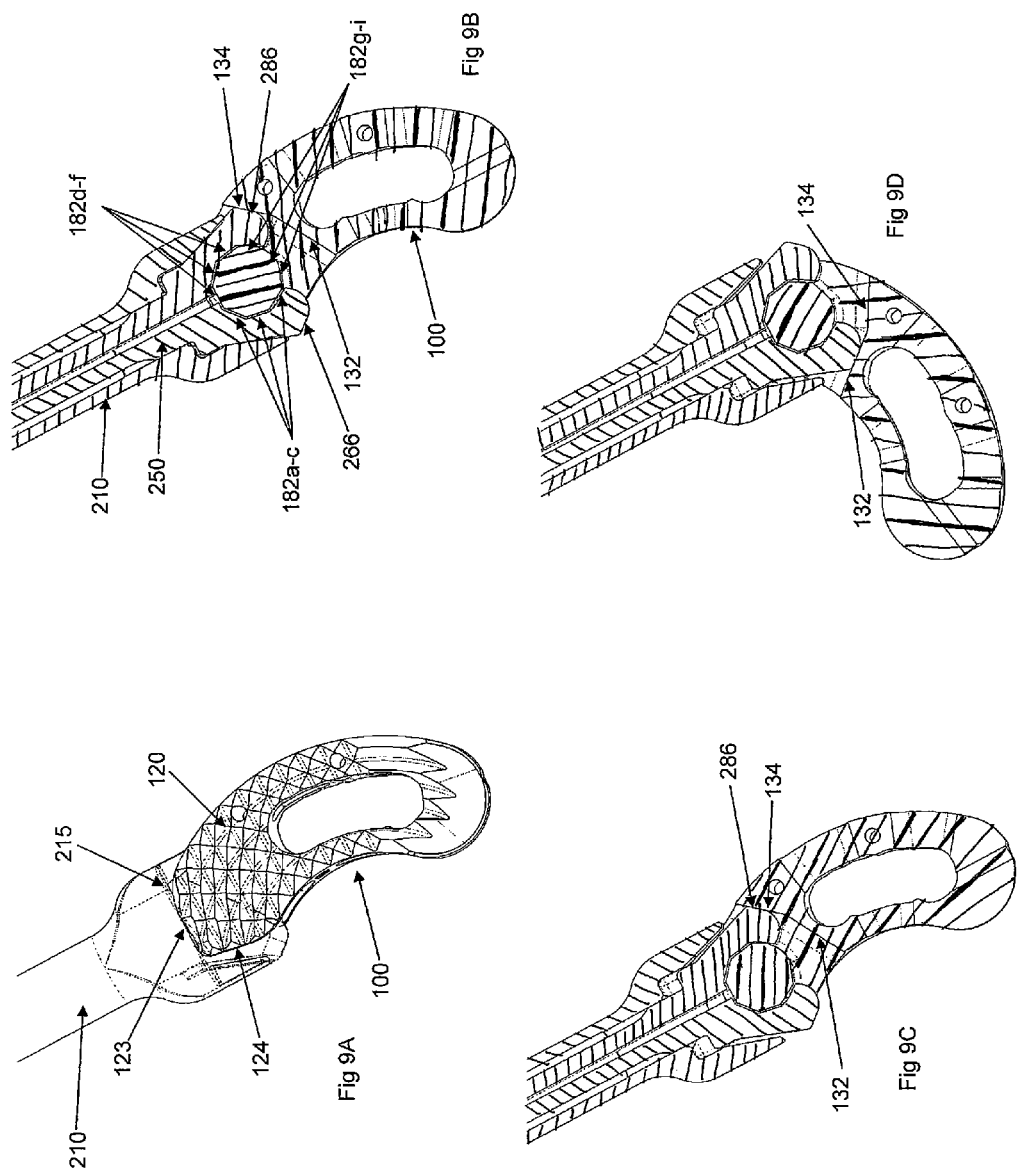

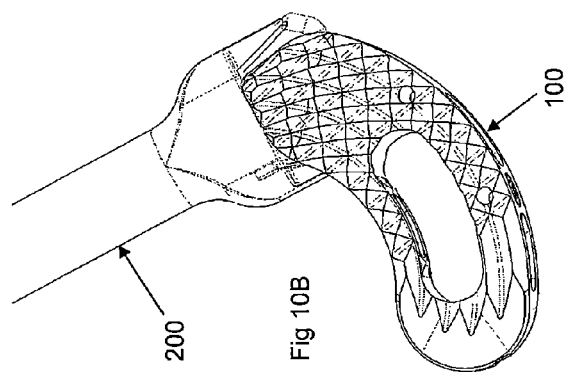
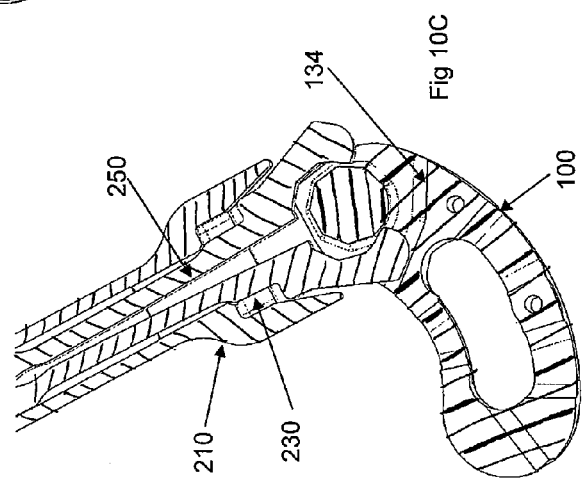
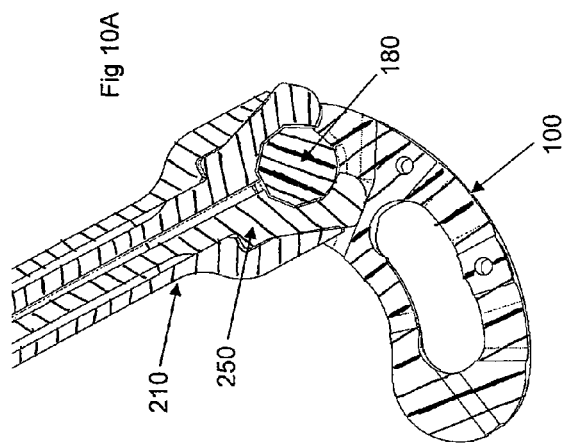

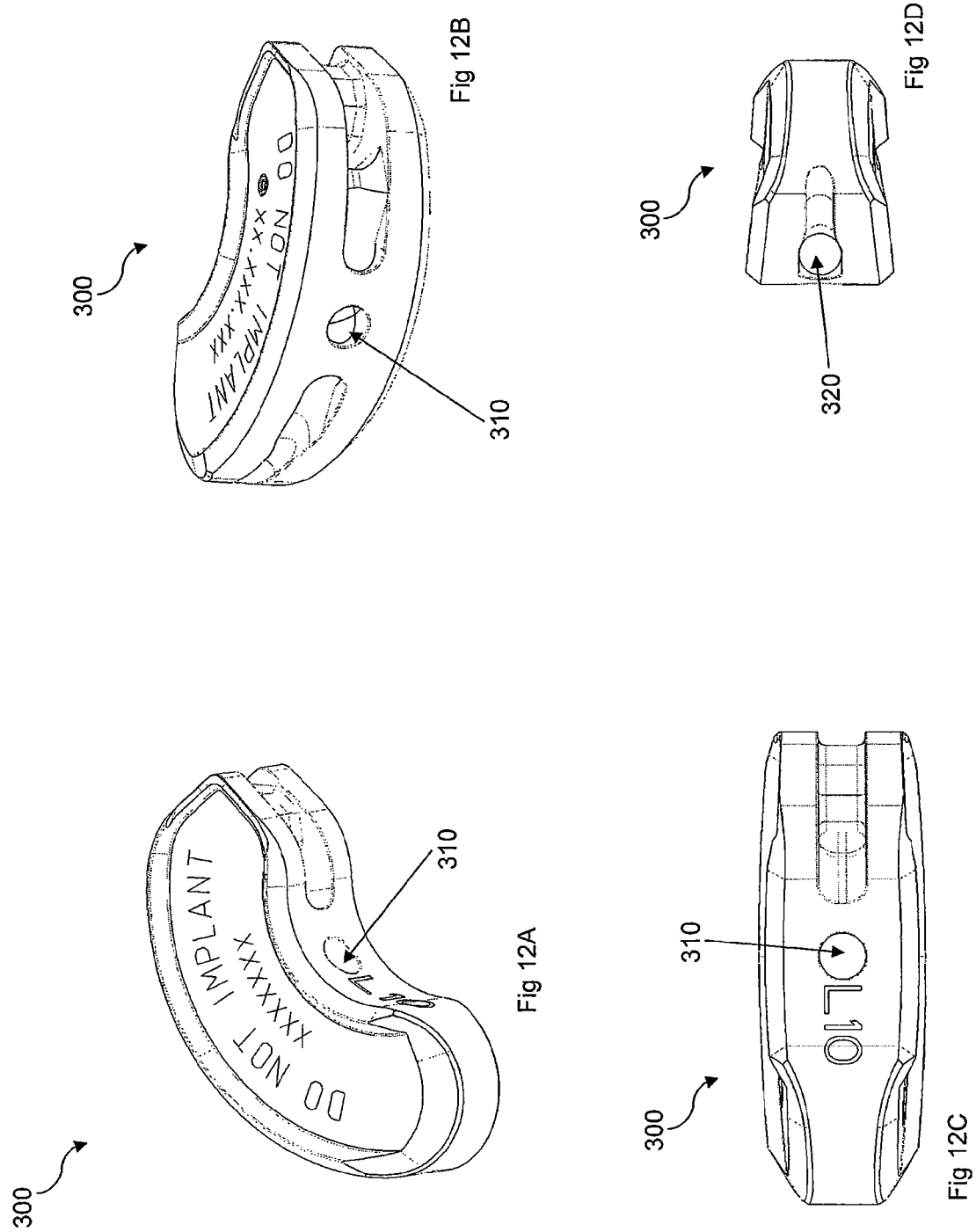

SELF-PIVOTING SPINAL IMPLANT AND ASSOCIATED INSTRUMENTATION

BACKGROUND OF THE INVENTION

The unilateral transforaminal insertion of an interbody spacer for lumbar spinal fusion presents challenges to the surgeon tasked with the procedure due to the curved manipulation path that the implant must undergo once it enters the disc space. The procedure presents a further challenge of coupling the implant to the inserter instrument while allowing the implant a limited amount of rotation or articulation to follow the desired path. These challenges also present themselves to other angular unilateral approaches to the spine, in which the initial access corridor is linear yet, once the implant enters the disc space, the implant must be manipulated or articulated along a curved path. Conventional transforaminal lateral interbody fusion (TLIF) implants, for example, are inserted using a combination of a linear insertion path and a hammering of the implant into the desired position using pushers that provide the desired anterior positioning of the implant. Alternately, a stepwise straight hammering process alternating with an active turning technique is often used to manipulate the implant from the entry position to the final desired position. The conventional TLIF and other angular unilateral systems and insertion methods fail to provide implants, instrumentation, and methods that allow the implant to be easily inserted to its final desired position within the disc space.

It is therefore desired to provide a spinal implant and associated instrument and method that improves the ease with which the implant may be manipulated during insertion or once within the disc space.

BRIEF SUMMARY OF THE INVENTION

Briefly stated, a first embodiment of the present invention comprises an intervertebral implant including an insertion end, an opposing engagement end, and first and second opposed main surfaces configured to contact respective adjacent vertebral endplates. Each of the first and second main surfaces has an anterior edge, a posterior edge, and extends between the insertion and engagement ends. An anterior wall is formed between the first and second main surfaces and along the anterior edges thereof. A posterior wall is formed between the first and second main surfaces and along the posterior edges thereof. The anterior wall and the posterior wall converge at the insertion and engagement ends. A slot is formed at the engagement end and extends continuously between and at least partially along the anterior and posterior walls. A post is positioned within the slot, spaced from at least one of the anterior and posterior walls and extending at least partially between the first and second main surfaces. The post includes a plurality of exposed facets and is configured for engagement with a pivotable insertion instrument.

Another embodiment of the present invention comprises an intervertebral implant including an insertion end, an opposing engagement end, and first and second opposed main surfaces configured to contact respective adjacent vertebral endplates. Each of the first and second main surfaces has an anterior edge, a posterior edge, and extends between the insertion and engagement ends. Each anterior edge has a generally linear portion proximate the engagement end and a generally concave portion, and each posterior edge has a generally linear portion proximate the engagement end and a generally convex portion. The generally linear portion of the anterior edge converges with the generally linear portion of the posterior edge at the engagement end for each of the first and second main surfaces. An anterior wall is formed between the first and second main surfaces and along the anterior edges thereof. A posterior wall is formed between the first and second main surfaces and along the posterior edges thereof. The anterior wall and the posterior wall converge at the insertion and engagement ends. A slot is formed at the engagement end and extends continuously between and at least partially along the anterior and posterior walls. A post is positioned within the slot, spaced from at least one of the anterior and posterior walls and extending at least partially between the first and second main surfaces. The post includes a plurality of exposed facets and is configured for engagement with a pivotable insertion instrument.

Still another embodiment of the present invention comprises an intervertebral implant including an insertion end, an opposing engagement end, and first and second opposed main surfaces configured to contact respective adjacent vertebral endplates. Each of the first and second main surfaces has an anterior edge, a posterior edge, and extends between the insertion and engagement ends. Each anterior edge is generally concave and each posterior edge is generally convex. An anterior wall is formed between the first and second main surfaces and along the anterior edges thereof. A posterior wall is formed between the first and second main surfaces and along the posterior edges thereof. The anterior wall and the posterior wall converge at the insertion and engagement ends. A slot is formed at the engagement end and extends continuously between and at least partially along the anterior and posterior walls. A post is positioned within the slot, spaced from the anterior and posterior walls and extending at least partially between the first and second main surfaces. The post includes a plurality of facets disposed around an entire periphery thereof and is configured for engagement with a pivotable insertion instrument. At least one abutment surface is disposed within the slot distally from the post. The at least one abutment surface limits rotation of the implant about the post when the post is engaged with the pivotable insertion instrument.

Yet another embodiment of the present invention comprises an intervertebral implant including an insertion end, an opposing engagement end, and first and second opposed main surfaces configured to contact respective adjacent vertebral endplates. Each of the first and second main surfaces has an anterior edge, a posterior edge, and extends between the insertion and engagement ends. Each anterior edge is generally concave and each posterior edge is generally convex. An axial bore is formed between the anterior and posterior edges and extends between the first and second main surfaces. An anterior wall is formed between the first and second main surfaces and along the anterior edges thereof. A posterior wall is formed between the first and second main surfaces and along the posterior edges thereof. The anterior wall and the posterior wall converge at the insertion and engagement ends. A slot is formed at the engagement end and extends at least partially along the anterior and posterior walls. A post is positioned within the slot and extends at least partially between the first and second main surfaces. The post includes a plurality of facets and is configured for engagement with a pivotable insertion instrument. The intervertebral implant also includes a plurality of markers. At least one of the markers extends between the first and second main surfaces within one of the anterior and posterior walls. At least one other of the markers is disposed generally transverse to the at least one of the markers and extends from the insertion end toward the axial bore.

A still further embodiment of the present invention comprises a method for implanting an intervertebral implant into a disc space disposed between first and second endplates of adjacent vertebral bodies of a patient. The method includes providing an access corridor to a spinal level in need, removing at least a portion of disc material between the adjacent vertebra, and providing an interbody spacer implant. The implant includes an insertion end, an opposing engagement end, and first and second opposed main surfaces configured to contact the respective first and second vertebral endplates. Each of the first and second main surfaces has an anterior edge, a posterior edge, and extends between the insertion and engagement ends. Each anterior edge is generally concave and each posterior edge is generally convex. Each of the first and second main surfaces includes a plurality of curved parallel ridges protruding from the respective surface and extending from the insertion end to the engagement end. Each of the plurality of parallel ridges includes a plurality of teeth. An anterior wall is formed between the first and second main surfaces and along the anterior edges thereof. A posterior wall is formed between the first and second main surfaces and along the posterior edges thereof. The anterior wall and the posterior wall converge at the insertion and engagement ends. A slot is formed at the engagement end and extends continuously between and at least partially along the anterior and posterior walls. A post is positioned within the slot, spaced from at least one of the anterior and posterior walls and extending at least partially between the first and second main surfaces. The post includes a plurality of exposed facets and is configured for engagement with a pivotable insertion instrument. The method also includes providing an insertion instrument. The instrument includes a proximal end, a distal end, and a longitudinal axis therebetween, and an inner member and an outer member. The inner member is movable along the longitudinal axis with respect to the outer member. The inner member has a grasping portion at the distal end. The grasping portion includes a plurality of facet surfaces configured for engagement with the plurality of the post facets. The method also includes inserting the grasping portion of the instrument into the slot of the implant such that the grasping portion surrounds the post, engaging the post of the implant with the grasping portion of the instrument such that the post is rotationally fixed with respect to the grasping portion, inserting the implant using the instrument through the access corridor until at least the insertion end is introduced into the at least partially cleared out disc space and such that the at least a portion of the ridges of the first and second main surfaces contact the first and second verebtral endplates, respectively, adjusting the instrument such that the post of the implant remains engaged with the grasping portion of the instrument but rotation of the post is permitted within the grasping portion, delivering impaction forces to the proximal end of the instrument such that the post of the implant articulates with respect to the grasping portion of the instrument and the implant is guided by vertebral rails into a desired position, releasing the post of the implant from the grasping portion of the instrument, and withdrawing the instrument through the access corridor.

Yet another embodiment of the present invention comprises a system for spine surgery at a disc space disposed between first and second endplates of adjacent vertebral bodies of a patient. The system includes an intervertebral implant including an insertion end and an opposing engagement end. First and second opposed main surfaces are configured to contact respective adjacent vertebral endplates. Each of the first and second main surfaces has an anterior edge, a posterior edge, and extends between the insertion and engagement ends. An anterior wall is formed between the first and second main surfaces and along the anterior edges thereof. A posterior wall is formed between the first and second main surfaces and along the posterior edges thereof. The anterior wall and the posterior wall converge at the insertion and engagement ends. A slot is formed at the engagement end and extends continuously between and at least partially along the anterior and posterior walls. A post is positioned within the slot, spaced from at least one of the anterior and posterior walls and extending at least partially between the first and second main surfaces. The post includes a plurality of exposed facets. A trial implant includes an insertion end and an opposing engagement end. First and second opposed main surfaces are configured to contact respective adjacent vertebral endplates. Each of the first and second main surfaces has an anterior edge, a posterior edge, and extends between the insertion and engagement ends. An anterior wall is formed between the first and second main surfaces and along the anterior edges thereof. A posterior wall is formed between the first and second main surfaces and along the posterior edges thereof. The anterior wall and the posterior wall converge at the insertion and engagement ends. A slot is formed at the engagement end and extends continuously between and at least partially along the anterior and posterior walls. A post is positioned within the slot, spaced from at least one of the anterior and posterior walls and extending at least partially between the first and second main surfaces. The post includes a plurality of exposed facets. An insertion instrument includes a proximal end, a distal end, a longitudinal axis therebetween, an inner member, and an outer member. The inner member is translatable with respect to the outer member along the longitudinal axis and has a grasping portion at the distal end. The grasping portion includes a plurality of facet surfaces engagable with the plurality of the post facets of the intervertebral implant and the trial implant. The instrument has a first configuration in which the grasping portion assumes an open configuration for allowing coupling of the instrument to the post of one of the intervertebral implant and the trial implant, a second configuration in which the instrument is securely coupled to the post of one of the intervertebral implant and the trial implant while allowing the post to rotate within the grasping portion under a given force, and a third configuration wherein the instrument is securely coupled to the post of one of the intervertebral implant and the trial implant while preventing rotation of the post with respect to the grasping portion.

BRIEF DESCRIPTION OF THE SEVERAL VIEWS OF THE DRAWINGS

The foregoing summary, as well as the following detailed description of preferred embodiments of the instrument of the present application, will be better understood when read in conjunction with the appended drawings. For the purposes of illustrating the self-pivoting spinal implant and the associated instrumentation of the present application, there is shown in the drawings preferred embodiments. It should be understood, however, that the application is not limited to the precise arrangements and instrumentalities shown. In the drawings:

FIG. 7 is a partial front perspective cross-sectional view of an inserter instrument in accordance with a first preferred embodiment of the present invention, the inserter instrument shown in open configuration;

FIG. 8B is a partial front perspective view of the inserter instrument of FIG. 7 in the open configuration;

FIG. 9A is a top plan view of the inserter instrument of FIG. 7 in an initial articulation position and in a finally locked configuration;

FIG. 9B is a cross-sectional view of the inserter instrument of FIG. 7 in the initial articulation position and in the finally locked configuration;

FIG. 9C is a cross-sectional view of the inserter instrument of FIG. 7 in the initial articulation position and in a provisionally locked configuration;

FIG. 9D is a cross-sectional view of the inserter instrument of FIG. 7 in a final articulation position and in the provisionally locked configuration;

FIG. 10A is a cross-sectional view of the inserter instrument of FIG. 7 in the final articulation position and in the finally locked configuration;

FIG. 10B is a top plan view of the inserter instrument of FIG. 7 in the final articulation position and in the finally locked configuration;

FIG. 10C is a cross-sectional view of the inserter instrument of FIG. 7 in the final articulation position and in the open configuration;

FIG. 12A is a rear perspective view of a trial implant in accordance with one embodiment of the present invention;

FIG. 12B front perspective view of the trial implant of FIG. 12A;

FIG. 12C is a rear elevational view of the trial implant of FIG. 12A; and

FIG. 12D is a left side elevational view of the trial implant of FIG. 12A.

DETAILED DESCRIPTION OF THE INVENTION

Figure 1:
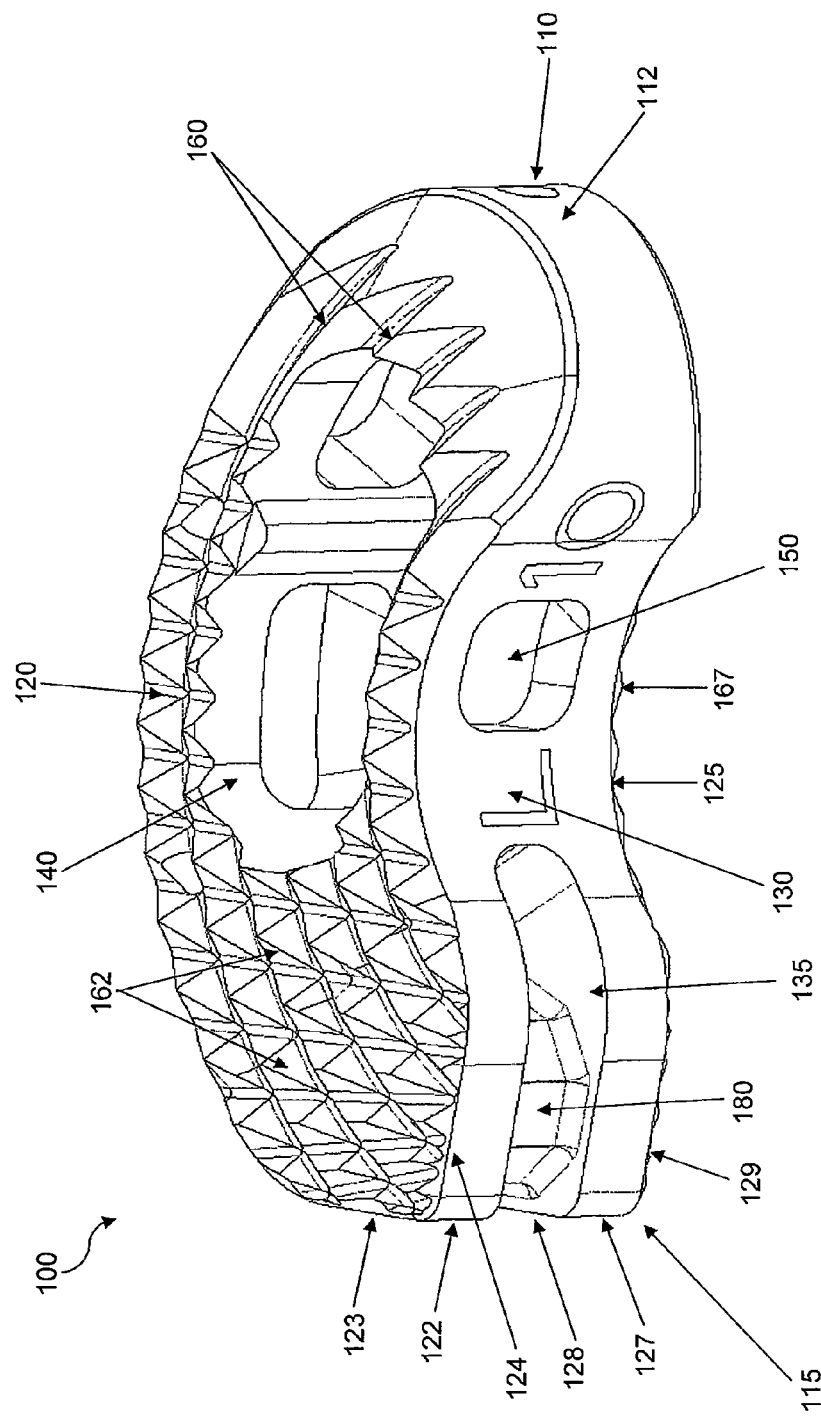
FIG. 1 is a rear perspective view of a self-pivoting TLIF implant in accordance with a first preferred embodiment of the present invention.
Figure 2:
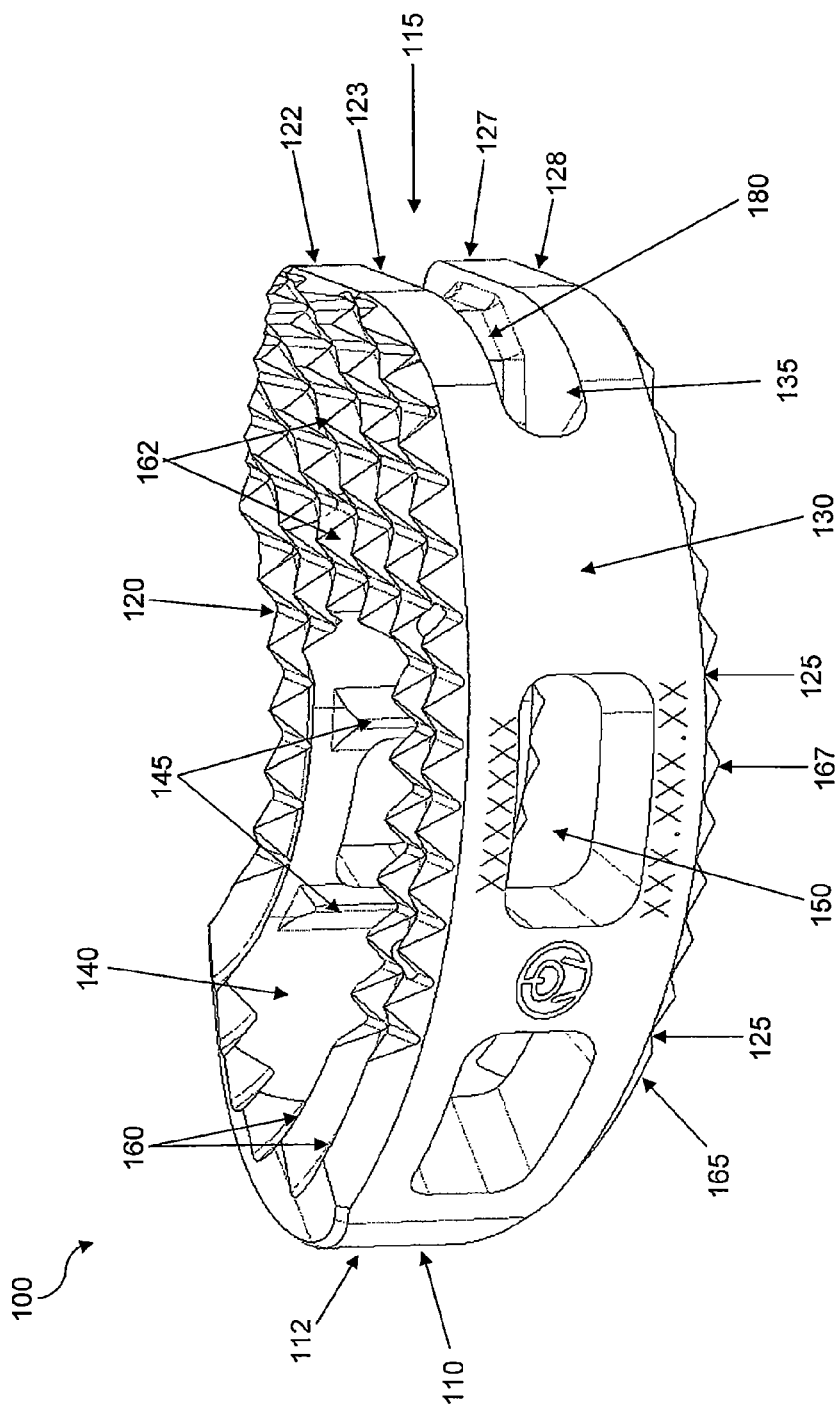
FIG. 2 is a front perspective view of the self-pivoting TLIF implant of FIG. 1.

Certain terminology is used in the following description for convenience only and is not limiting. The words "right," "left," "lower," and "upper" designate directions in the drawings to which reference is made. The words "inwardly" or "distally" and "outwardly" or "proximally" refer to directions toward and away from, respectively, the patient's body, or the geometric center of the interbody spacer implant and related parts thereof. The words, "anterior," "posterior," "superior," "inferior," and related words and/or phrases designate preferred positions and orientations in the human body to which reference is made and are not meant to be limiting. The terminology includes the above-listed words, derivatives thereof and words of similar import.

Referring to FIGS. 1-6, a TLIF spacer 100 is provided that includes an insertion end 110 and an engagement end 115, the insertion end 110 preferably forming a bullet-nose 112 or having some other tapered geometry for enhancing the ease of insertion and/or for applying a distraction force to the two vertebral bodies between which the implant 100 is configured to be inserted. The implant 100 further includes a first main or superior surface 120 that is configured for contacting the inferior endplate of a superior vertebral body and a second main or inferior surface 125 that is configured for contacting the superior endplate of an inferior vertebral body. One or more walls 130 on anterior and posterior sides extend between the superior and inferior surfaces 120, 125 and enclose an axial bore 140 that extends through both the superior and inferior surfaces 120, 125. The axial bore 140 is configured to house a bone graft 190 or other fusion enhancing material.

One or more lateral windows 150 are disposed in the walls 130 and provide a visibility window for observing the fusion occurring between the vertebral bodies and enhancing the vascularization of the bone graft 190 disposed within the axial bore 140 to assist fusion, as well as to increase the volume of the axial bore 140. One or more surface features 145 are provided along interior portions of the walls 130 that form the axial bore 140 to assist in securing the bone graft 190 within the axial bore 140. The features 145 can assume the form of one or more ridges extending through the axial bore 140 along the cranial-caudal direction, grooves, or other surface texturing that enhances the friction between the bone graft 190 and the interior of the walls 130 that form the axial bore 140.

In a first preferred embodiment, the TLIF spacer 100 has a kidney bean or banana shape having a curvilinear geometry between its insertion and engagement ends 110, 115. This shape may be accomplished by having an anterior edge of the superior and inferior surfaces 120, 125 along with the anterior wall 130 be generally concave and a posterior edge of the superior and inferior surfaces 120, 125 along with the posterior wall 130 be generally convex. However, a variety of geometries may be utilized for the implant 100, depending on the desired amount of surface contact between the endplates of the vertebral bodies and the implant 100, the number of implants 100 desired to be implanted within the disc space (e.g., one or two), the approach chosen for the surgery, the desired location of the implant within the disc space (anterior or posterior), or the like. Disposed upon the superior surface 120 adjacent the insertion end 110 are a plurality of curvilinear superior ridges 160 that are arranged parallel to one another along the curvature of the TLIF implant 100.

In a first preferred embodiment, the superior ridges 160 include two linearly sloped surfaces that meet to form an apex. As the superior ridges 160 extend along their curvilinear path away from the insertion end 110, the superior ridges 160 are interrupted to form a plurality of superior teeth 162. The superior teeth 162 are disposed at the engagement end 115 and along at least a portion of anterior and posterior sides of the axial bore 140. Similarly, disposed upon the inferior surface 125 adjacent the insertion end 110 is a plurality of curvilinear inferior ridges 165 that are arranged parallel to one another along the curvature of the TLIF implant 100. As the inferior ridges 165 extend along their curvilinear path away from the insertion end 110, the inferior ridges 165 are interrupted to form a plurality of inferior teeth 167. The inferior teeth 167 are disposed at the engagement end 115 and on the anterior and posterior sides of the axial bore 140. The superior and inferior ridges 160, 165 guide the insertion of the TLIF implant 100 under the compressive forces of the adjacent vertebral bodies, while the superior and inferior teeth 162, 167 assist in the primary fixation of the TLIF implant 100.

Figure 3:
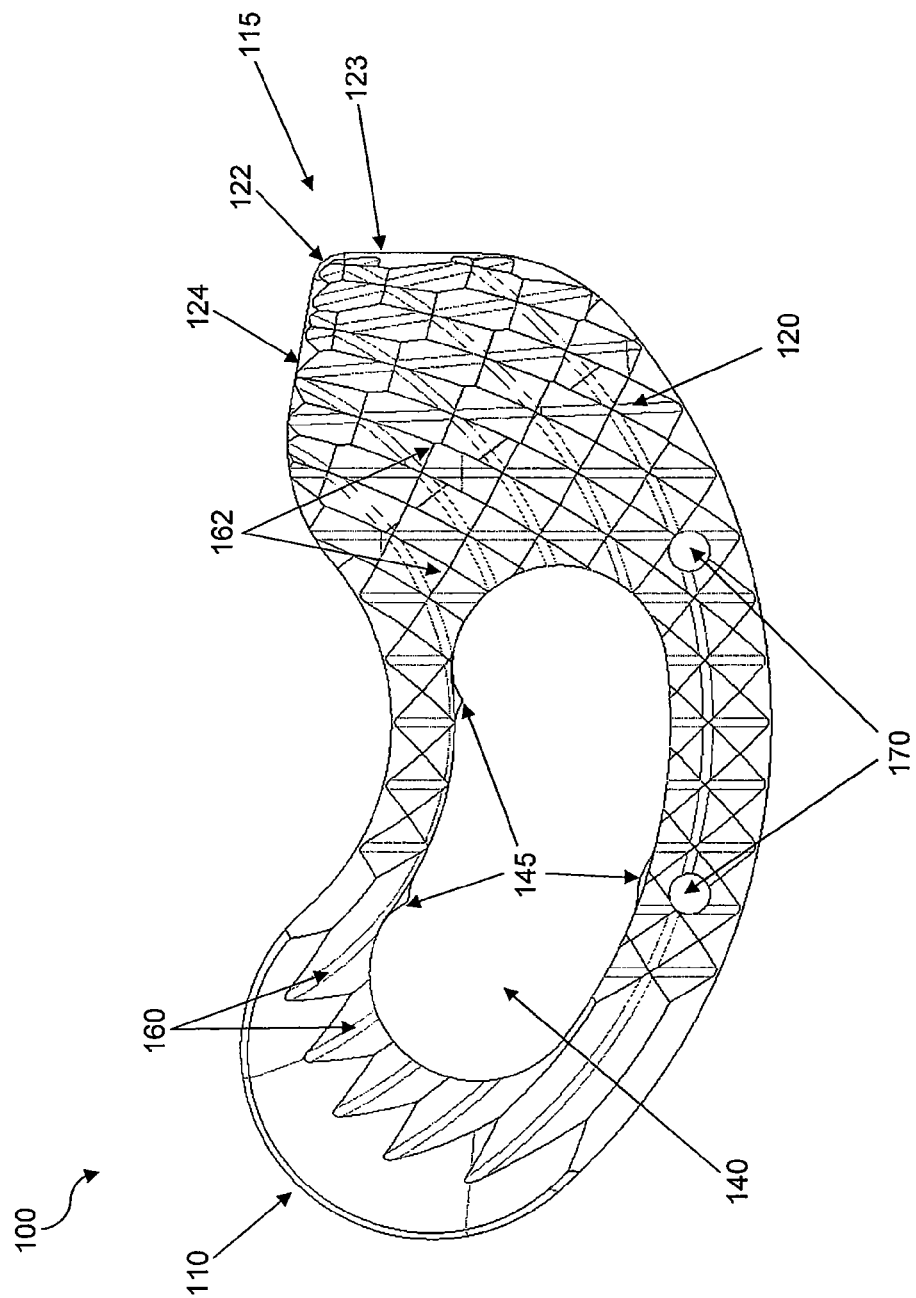
FIG. 3 is a top plan view of the self-pivoting TLIF implant of FIG. 1.
Figure 4:
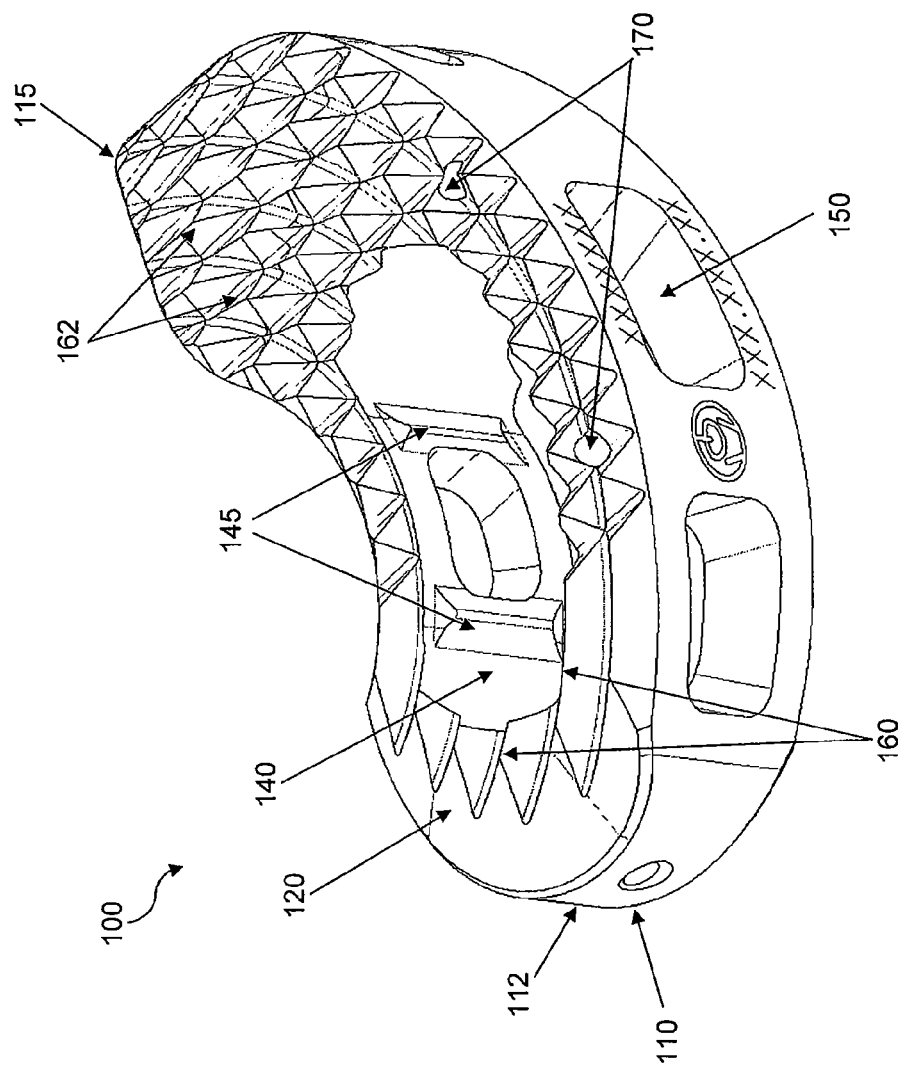
FIG. 4 is a front and left side perspective view of the self-pivoting TLIF implant of FIG. 1.
Figure 5:
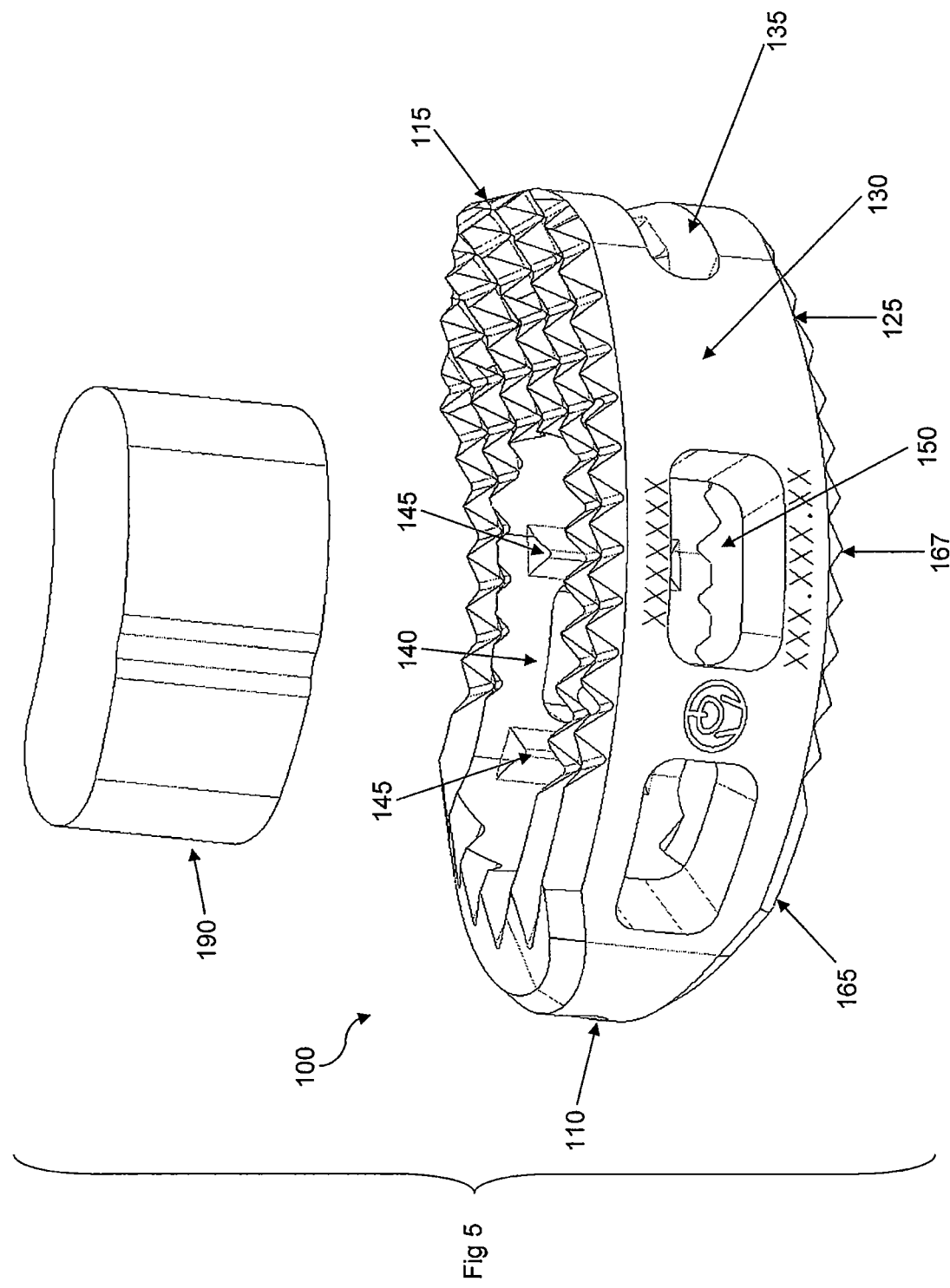
FIG. 5 is a front perspective view of the self-pivoting TLIF implant of FIG. 1 and a bone growth promoting material configured for insertion into the implant.
Figure 6:
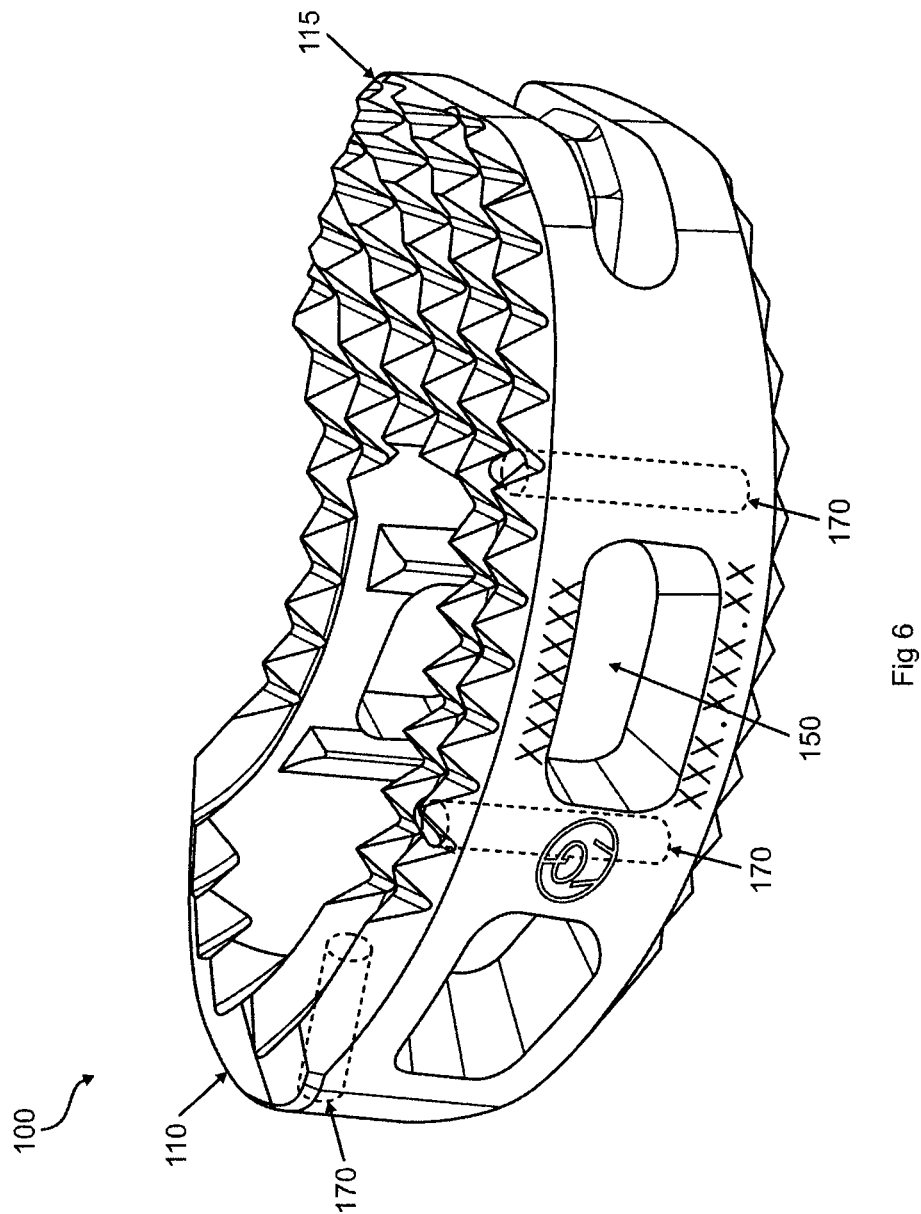
FIG. 6 is a front perspective view of the self-pivoting TLIF implant of FIG. 1 showing a preferred arrangement of radiopaque markers.

Referring to FIGS. 3, 4, and 6, one or more radiopaque markers 170, made from material capable of radiographical imaging, such as pins or beads of stainless steel, titanium, tantalum, titanium-aluminum-niobium (TAN), or the like, are included in the TLIF implant 100 for enabling visualization and controlling of the position of the TLIF implant 100 during and after insertion into the disc space. In a first preferred embodiment, the markers 170 are elongated and include a first marker 170A, a second marker 170B, and a third marker 170C. The first and second markers 170A, 170B are disposed in the cranial-caudal direction on either side of the lateral window 150 within the anterior wall 130 of the implant 100. The third marker 170C is disposed proximate the insertion end 110, with a longitudinal axis thereof extending from the insertion end 110 toward the axial bore 140.

The engagement end 115 is characterized by the absence of the walls 130 extending fully between the superior and inferior surfaces 120, 125. That is, a slot 135 is formed at the engagement end 115 that extends continuously between and at least partially along the anterior and posterior walls 130. A post 180 is positioned within the slot 135, which is spaced apart from the anterior and posterior walls 130 and extends at least partially between the superior and inferior surfaces 120, 125 and serves as an instrument engagement feature. Adequate space is provided by the slot 135 for the engagement portion of an instrument 200 (FIG. 7) to engage the post 180. As shown in FIGS. 9 and 10, within the implant 100, the walls 130 disposed between the axial bore 140 and the post 180 include first and second mating surfaces 132, 134 facing the post 180 between which an obtuse angle is formed for providing a pair of mechanical stops to the range of allowable articulation of the implant 100 with respect to the instrument 200. The first and second mating surfaces 132, 134 are preferably linear surfaces, but may also be curved or the like. Alternatively, stop pins or the like may be used to limit articulation of the implant 100.

Referring now to FIGS. 9 and 10, in a first preferred embodiment, the post 180 is polygonal in cross-section and includes nine exposed facets 182a-182i arranged around an entire periphery thereof and extending in the cranial-caudal direction between the superior and inferior surfaces 120, 125. The facets 182a-182i are configured to enhance the engagement and interaction between the instrument 200 and the implant 100 during the insertion of the implant 100. Preferably, seven of the facets 182a-182f, 182i are flat surfaces, while the remaining two facets 182g-182h are curved surfaces. In an alternate embodiment, the post 180 may include a different polygonal number of facets 182. In yet another alternate embodiment, the post 180 can be cylindrical and thus include zero facets 182, and may include other features for governing the articulation of the implant 100 with respect to the instrument 200 during its insertion. For example, the post 180 can include dimples, teeth, surface texturing, grooves, or the like.

Referring now to FIGS. 1-5 and 7, the engagement end 115 of the superior surface 120 terminates in a superior corner 122, which includes superior first and second flat segments 123, 124 originating near the post 180 and converging at an angle disposed proximate the engagement end 115 of the implant 100. Similarly, the engagement end 115 of the inferior surface 125 terminates in an inferior corner 127, which include inferior first and second flat segments 128, 129 originating near the post 180 and converging terminating at an angle disposed proximate the engagement end 115 of the implant 100. The superior first flat segment 123 and the inferior first flat segment 128 are configured to be engagable by a portion of the instrument 200, as is described in detail below, to provide a toggle-free connection, as are the superior second flat segment 124 and the inferior second flat segment 129. The rims of both the superior and inferior corner segments 122, 127 have a width extending a short distance from the superior and inferior surfaces 120, 125 toward the center of the implant 100. The surfaces of the rims are also flat for enhancing the interaction between the instrument 200 and the implant 100. The implant 100 can be formed from a variety of biocompatible materials, including but not limited to titanium, stainless steel, allograft bone, or polymers such as polyaryletheretherketone (PEEK) and polyetherketoneketone (PEKK), titanfoam, porous PEEK, or the like.

Figure 8A:
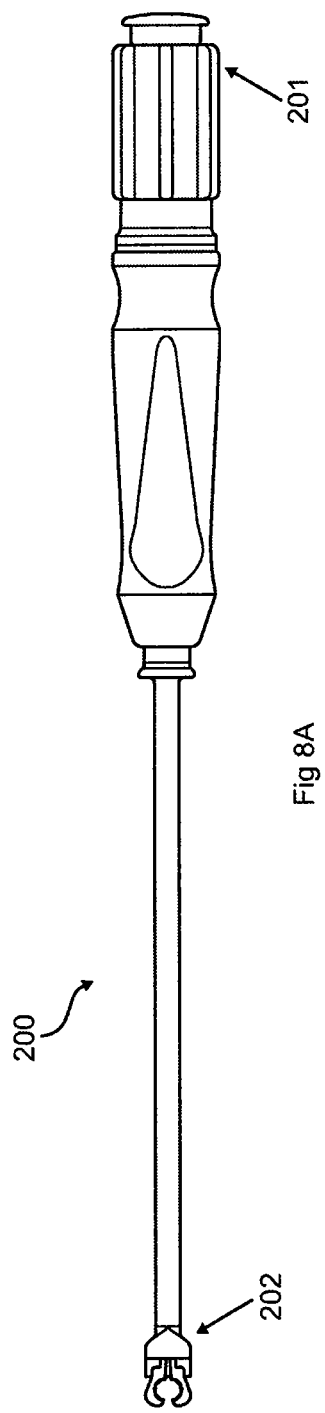
FIG. 8A is a top plan view of the inserter instrument of FIG. 7.

Referring to FIGS. 7-8, an instrument 200 is provided that includes a longitudinal axis extending between a proximal end 201 and a distal end 202. The instrument 200 includes an elongated cannulated outer member 210 that surrounds an elongated inner member 250. The inner member 250 is configured to be translatable with respect to the outer member 210 along the longitudinal axis. Alternatively, the instrument 200 can be configured such that the outer member 210 is translatable with respect to the inner member 250 along the longitudinal axis to perform in the same manner. The proximal end of the outer member 210 includes a handle portion (not shown) and an actuation mechanism (not shown) for translating the inner member 250 with respect to the outer member 210. The distal end of the outer member 210 includes an outer member first arm 220 and an outer member second arm 240 that are separated by a gap 230 that forms the distal portion of the cannula. The gap 230 includes a pair of laterally-oriented surfaces 232 on either side of the cannula disposed at the proximal end of the outer member first and second arms 220, 240. The laterally-oriented surfaces 232 serve as a stop to the retraction of the inner member 250 with respect to the outer member 210. The interior surface of the first arm 220 includes an outer member first arm interior linear taper 222 disposed distal to an outer member first arm interior straight portion 224, while the interior surface of the second arm 240 includes an outer member second arm interior linear taper 242 disposed distal to an outer member second arm interior straight portion 244. The first and second arm interior linear tapers 222, 242 combine to form two wedging surfaces.

A laterally-extending superior exterior flat surface 215 of the outer member 210 is disposed between the distal ends of the outer member first and second arms 220, 240 and the laterally-oriented surfaces 232. Similarly, a laterally-extending inferior exterior flat surface 216 of the outer member 210 is disposed between the distal ends of the outer member first and second arms 220, 240 and the laterally-oriented surfaces 232. The laterally-extending superior exterior flat surface 215 and the laterally-extending inferior exterior flat surface 216 are configured to serve as stops to prevent overarticulation of the implant 100 by abutting the superior and inferior first flat segments 123, 128 at one end of the articulation range and interacting with the superior and inferior second flat segments 124, 129 at the other end of the articulation range, as is described in detail below. The laterally-extending superior and inferior exterior flat surfaces 215, 216 also abut against the superior and inferior first flat segments 123, 128 of the implant 100, or against the superior and inferior second flat segments 124, 129 of the implant 100, during a portion of the implant insertion procedure.

The inner member 250 includes at its distal end a grasping portion 255 an inner member first arm 260 and an inner member second arm 280 separated by a split 270 that extends through the middle of the inner member 250 along the longitudinal axis from the grasping portion 255 toward the proximal end. The interior surface of the grasping portion 255 includes a plurality of engagement surfaces 257 that are configured to complementarily match the polygonal cross sectional geometry of the post 180 of the implant 100 and, thus, engage several of the plurality of facets 182a-182i. In a first preferred embodiment, there are seven engagement surfaces 257a-257g that are configured to engage seven of the nine facets 182a-182i of the post 180. Configured to interact with the interior surfaces of the outer member first and second arms 220, 240, the exterior surface of the inner member first arm 260 includes an inner member first arm exterior linear taper 262 disposed distal to an inner member first arm exterior straight portion 264, while the exterior surface of the inner member second arm 280 includes an inner member second arm exterior linear taper 282 disposed distal to an inner member second arm exterior straight portion 284. Disposed between the inner member first arm exterior linear taper 262 and the distal tip of the inner member first arm 260 is an inner member first arm second exterior linear taper 266.

Similarly, disposed between the inner member second arm exterior linear taper 282 and the distal tip of the inner member second arm 280 is an inner member second arm second exterior linear taper 286. Further, an inner member first arm laterally-oriented flat surface 265 and an inner member second arm laterally-oriented flat surface 285 are formed proximal to and adjacent the inner member first arm exterior straight portion 264 and the inner member second arm exterior straight portion 284, respectively, such that a pair of corners are formed therebetween, and such that the inner member first and second arm laterally-oriented flat surfaces 265, 285 face and abut with the laterally-oriented surfaces 232.

Referring to FIG. 12, a trial implant 300 is provided that includes geometry and surface features identical or similar to the implant 100 and further includes a lateral hole 310 and a longitudinal hole 320 and, therefore, a complete description of the trial implant is omitted for convenience only and is not limiting. The trial implant 300 is formed from a material that is visible under radiographic imaging, such as titanium, stainless steel, or the like. The lateral and longitudinal holes 310, 320, when viewed in conjunction with lateral and frontal X-rays, assist in the optimum positioning of the trial implant 300. The lateral holes 310 allow the surgeon to center the trial implant 300 with respect to the spinous processes of the vertebral bodies under fluoroscopy. The longitudinal hole 320 indicates whether the trial implant 300 has turned, in which case the surgeon will know that more disc material should preferably be removed. The lateral and longitudinal holes 310, 320 are shown as being generally circular or cylindrical in the preferred embodiment, but are not so limited. The lateral and longitudinal holes 310, 320 may have nearly any size and/or shape, such as rectangular, square, arrow-shaped, and/or triangular that permits visualization of the location of the trial implant 300 under imaging. In addition, the trial implant 300 is not limited to including the lateral and longitudinal holes 310, 320 or any holes, as location of the trial implant 300 may be visualized via markers or other features that are optically or machine viewable.

In operation, and in continuing reference to FIGS. 1-12, a spinal disc in need of repair or replacement is identified and an at least partial discectomy is performed, preferably via a unilateral transforaminal approach. The trial implant 300 is inserted and removed using the instrument 200 to gauge the appropriate size implant 100 for insertion into the disc space. The insertion and manipulation of the trial implant 300 using the instrument 200 is identical to the method of inserting and manipulating the implant 100 using the instrument 200, as described below. The lateral and longitudinal holes 310, 320 are viewed using lateral and/or frontal X-rays to confirm the appropriate position of the trial implant 300 within the disc space and an implant size is then chosen.

Thus, the trial implant 300 is used for more than simply measuring the height between the vertebral bodies. Since the trial implant 300 articulates and is inserted to the same desired position as the final implant 100, the trial implant 300 may be used to determine whether the desired position of the implant 100 is reachable, whether enough disc material has been removed, and the like.

The bone graft 190 is then inserted into the axial bore 140 and secured therein via the surface features 145 (if not already preassembled thereto) and the implant 100 is then coupled to the instrument 200 by distracting the outer member 210 with respect to the inner member 250 via the manipulation of the actuation mechanism (not shown) such that the instrument 200 assumes an open configuration, as seen in FIGS. 7, 8, and 10C. The grasping portion 255 is then centered around the post 180 and the inner member 250 is partially retracted with respect to the outer member 210 via the manipulation of the actuation mechanism, thereby forcing the pair of corners formed between the inner member first and second arm exterior straight portions 264, 284 and the inner member first and second arm laterally-oriented flat surfaces 265, 285 to slidingly bear against the outer member first and second arm interior linear tapers 222, 242 until the inner member first and second arm exterior straight portions 264, 284 come to bear against the outer member first and second arm interior straight portions 224, 244, while providing the gap 230 between the inner member first and second arm laterally-oriented flat surfaces 265, 285 and the laterally-oriented surfaces 232. Consequently, the grasping portion 255 is collapsed around the post 180 such that the engagement surfaces 257a-g come into contact against the plurality of facets 182a-i of the post 180 and such that the post 180 is provisionally captured by the grasping portion 255, as shown in FIG. 9C, with the inner member first arm second exterior linear taper 286 bearing against the second linear surface 134.

In this provisionally locked configuration, the implant 100 is secured to the instrument but the post 180 is capable of rotation with respect to the grasping portion 255 but is prevented from exiting from the grasping portion 255. Final locking of the grasping portion 255 about the post 180, as shown in FIGS. 9A, 9B, 10A, and 10B, is achieved by fully retracting the inner member 250 with respect to the outer member 210 via the continued manipulation of the actuation mechanism, thereby forcing the outer member first arm interior linear taper 222 and the outer member second arm interior linear taper 242 to come to bear against the inner member first arm exterior linear taper 262 and the inner member second arm exterior linear taper 282, respectively, thereby closing the gap 230, and finally locking the implant 100 to the instrument 200 while preventing any portions of the inner member first and second arms 260, 280 from separating under force from one another across the split 270 due to the contact between the outer member first and second arm interior linear tapers 222, 242 and the inner member first and second arm exterior linear tapers 262, 282. In this finally locked configuration, the superior and inferior exterior flat surfaces 215, 216 contact the superior and inferior first flat segments 123, 128, respectively, the gap 230 is closed, the inner member first arm second exterior linear taper 286 still bears against the second linear surface 134, and the post 180 is incapable of rotating with respect to the grasping portion 255.

In the finally locked configuration, the handle portion of the instrument 200 is grasped and the insertion end 110 of the implant is inserted into the transforaminal window created during the discectomy procedure until the bullet nose 112 enters the disc space and begins to distract the adjacent vertebral bodies and the distal end of the superior and inferior ridges 160, 165 make contact with the inferior surface of the superior vertebral body and the superior surface of the inferior vertebral body, respectively. Gentle hammer blows or other impaction forces are administered to the proximal end 201 of the instrument 200 to urge the implant 100 at least partially into the disc space. Toggling is prevented between the implant 100 and the instrument 200 during the delivery of impaction forces due to the abutment of (1) the superior and inferior first flat segments 123, 128 with the superior and inferior exterior flat surfaces 215, 216, and/or (2) the second linear surface 134 with the first arm second linear taper 286 and/or (3) the plurality of facets 182a-i of the post 180 with the engagement surface 257a-f when the instrument 200 is in its finally locked configuration with respect to the implant 100. Any of these abutments alone or in combination preferably prevent toggling between the implant 100 and the instrument 200 in the finally locked configuration.

Figure 11B:
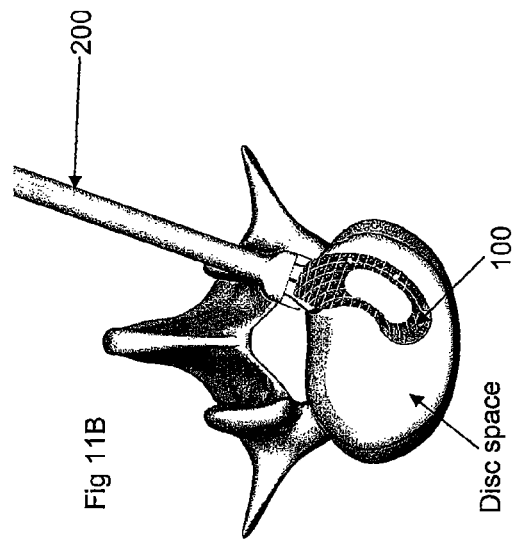
FIG. 11B is a top plan view, partially broken away, of a the implant and instrument of FIG. 11A in a second position.
Figure 11D:
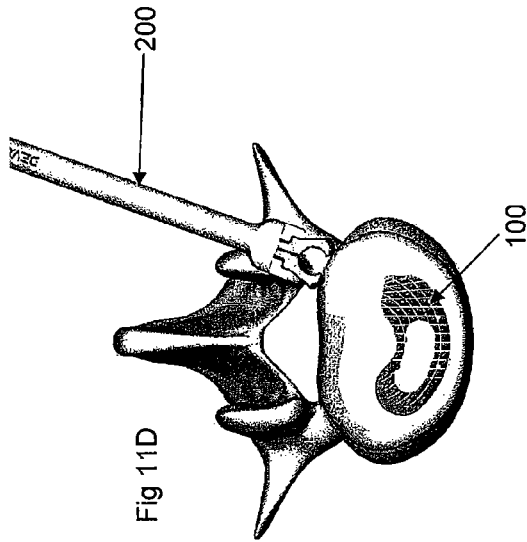
FIG. 11D is a top plan view of a the implant and instrument of FIG. 11C in a fourth position.
Figure 11A:
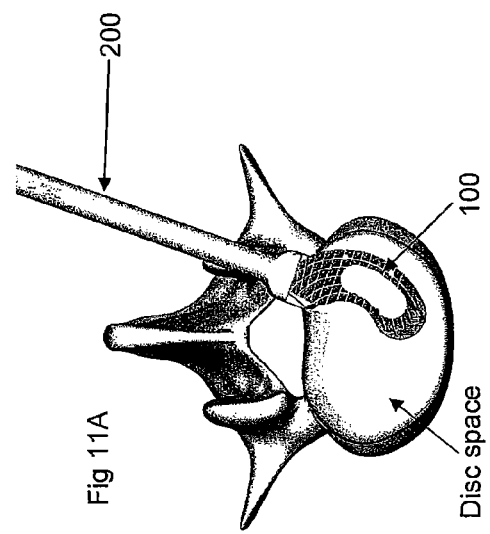
FIG. 11A is a top plan view, partially broken away, of one position of the implant of FIG. 1 and the instrument of FIG. 7 with respect to a disc space, partially broken away, as the implant is inserted therein.
Figure 11C:
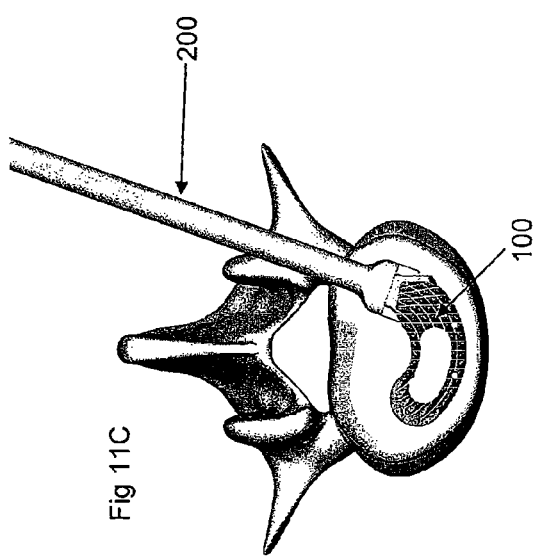
FIG. 11C is a top plan view, partially broken away, of a the implant and instrument of FIG. 11B in a third position.

Once the impaction forces drive the implant 100 along a linear path to a desired position within the disc space, as seen in FIG. 11A, with the instrument 200 finally locked to the implant 100, the inner member 250 is advanced with respect to the outer member 210 such that the instrument reassumes its provisionally locked configuration with respect to the implant 100, in which the implant 100 is coupled to the instrument but the post 180 is capable of rotation with respect to the grasping portion 255. At this point, additional gentle hammer blows or other impaction forces are administered to the proximal end of the instrument 200 and the superior and inferior ridges 160, 165 contact the endplates of the vertebral bodies to promote turning of the implant 100 and guide the path of insertion of the implant 100 as the insertion end 110 progresses into the disc space. As the superior and inferior ridges 160, 165 guide the implant 100 into the desired position within the disc space, the post 180 and, hence, the implant 100, rotates with respect to the grasping portion 255 within a range restricted by the stops provided by the interaction between the inner member second arm second exterior linear taper 286 bearing against the second linear surface 134 (the starting configuration of the insertion method) and the inner member first arm second exterior linear taper 266 bearing against the first linear surface 132 (at maximum angulation).

Throughout the entirety of the insertion process, the angle of the shaft of the instrument 200 with respect to the disc space is maintained constant, as all of the action performed to articulate the implant 100 is undertaken by the implant 100 itself as the gentle impaction forces drive the implant 100 into its desired final position guided by the superior and inferior ridges 160, 165, with no active turning of the implant necessary. Upon contact between the inner member first arm second exterior linear taper 266 and the first linear surface 132, the implant 100 is at or near its desired final positioning interior to the disc space. At this point, the implant 100 can be repositioned as necessary by again finally locking the implant 100 to the instrument 200, by retracting the inner member 250 distally with respect to the outer member 210, and manipulating the handle of the instrument 200 until the optimum final positioning of the implant 100 is achieved with respect to the disc space while viewing the position of the markers 170 under fluoroscopic imaging. The arrangement of the markers 170 enables a single radiographic image, e.g., a lateral image, to be used to determine the precise position of the implant 100 with respect to the disc space. The implant 100 is then released from the instrument 200 by manipulating the actuation mechanism until the instrument 200 assumes its open configuration, as described previously, and the grasping portion 255 no longer contacts the post 180. The compression forces between the vertebral endplates and the superior and inferior surfaces 120, 125 maintain the implant 100 in place as the instrument 200 is removed from the disc space and the patient's body.

The insertion and removal of the trial implant 300 may cause the formation of grooves in the adjacent endplates of the superior and inferior vertebral bodies due to the inclusion on the superior and inferior surfaces of the trial implant 300 of superior and inferior ridges that are identical to the superior and inferior ridges 160, 165 of the implant 100. The formation of such grooves in the adjacent endplates of the superior and inferior vertebral bodies, while not required for insertion of the implant 100, may assist in easing the insertion of the implant 100 using the instrument 200 via the guided mating of the superior and inferior ridges 160, 165 with the grooves formed previously by the trial implant 300.

While embodiments of the present invention are described herein with respect to an interbody spacer configured for insertion via a transforaminal path, a variety of implants may be utilized, such as total disc replacements and nucleus replacement devices, by simply configuring such implants to include an appropriately faceted post for an instrument engagement feature and, optionally, the stops and toggle-free bearing surfaces described herein. As such, the implant 100 is not limited to a banana or kidney bean shape, but may assume any geometry that can be accommodated within the disc space. Further, a range of angular approaches to the disc space may be utilized where an elongated implant is desired to be manipulated or pivoted once it has been delivered along a straight path into the disc space, such as posterior-lateral approaches, translateral, and direct lateral procedures.

In an alternate embodiment, the non-toggling interface between the implant 100 and the instrument 200 during the delivery of impaction forces that is provided by the interaction and abutment of the superior and inferior first flat segments 123, 128 with the laterally-extending superior and inferior exterior flat surfaces 215, 216, as well as the interaction and abutment of the superior and inferior second flat segments 124, 129 with the laterally-extending superior and inferior exterior flat surfaces 215, 216, can also be provided with non-linear abutment surfaces. As long as the surfaces mate or are able to abut one another when the instrument assumes its finally locked configuration, a non-toggling interface can be provided.

Similarly, the articulation stops that prevent overarticulation of the implant 100 with respect to the instrument 200 that are embodied by the first and second linear surfaces 132, 134, and the range of articulation provided by the obtuse angle disposed therebetween, can be provided by a variety of angles which can be tailored specifically to a desired articulation range for a given application, and therefore does not necessarily need to be obtuse. Further, the first and second linear surfaces 132, 134, as well as the inner member first and second arm second exterior linear tapers 266, 286 that are abutted thereagainst, need not be linear surfaces. Rather, any mating abutment surfaces will suffice between 132 and 266 and between 134 and 286 for the purposes of limiting the articulation range. Further, an embodiment may be envisioned in which the obtuse angle is removed between the first and second linear surfaces 132, 134 such that a single abutment surface is provided that can limit the range of articulation by being abuttable by both the first and second arm second exterior linear tapers 266, 286 and, further, does not need to be linear as long as it provides a mating abutment surface to the geometry chosen for the first and second arm second exterior linear tapers 266, 286.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

We claim:

1. An intervertebral implant comprising:
    an insertion end and an opposing engagement end;
    first and second opposed main surfaces configured to contact respective first and second vertebral endplates, each of the first and second main surfaces defining an anterior end, and a posterior end, and each of the first and second main surfaces disposed between the insertion and engagement ends;
    an anterior wall disposed between the first and second main surfaces, the anterior wall disposed along the anterior ends of the first and second main surfaces;
    a posterior wall disposed between the first and second main surfaces, the posterior wall disposed along the posterior ends of the first and second main surfaces, and the anterior wall and the posterior wall converging at the insertion and engagement ends;
    a slot defined at the engagement end, the slot continuously disposed between and at least partially along the anterior and posterior walls;
    a post positioned within the slot, the post spaced from at least one of the anterior or posterior walls, the post at least partially disposed between the first and second main surfaces, and the post defining a plurality of exposed facets, the plurality of exposed facets being configured to engage complementary facets of an insertion instrument so as to rotatably couple the post to the insertion instrument when the insertion instrument is engaged with the post; and
    an abutment surface disposed within the slot and spaced from the post, the abutment surface having a first portion and a second portion that is contiguous to the first portion, the first portion being angularly offset from the second portion, the first and second portions are configured to contact a surface of the insertion instrument when the post is engaged with the insertion instrument so as to prevent rotation of the intervertebral implant about the post.

2. The intervertebral implant of claim 1, wherein each anterior end is generally concave and each posterior end is generally convex.

3. The intervertebral implant of claim 2, wherein each of the first and second main surfaces includes a plurality of curved parallel ridges protruding from the respective surface and extending from the insertion end to the engagement end, each of the plurality of parallel ridges including a plurality of teeth.

4. The intervertebral implant of claim 1, wherein the anterior and posterior walls define a first height of the implant proximate the engagement end and a second height at the insertion end, the second height being less than the first height.

5. An intervertebral implant configured to be inserted between a first and second vertebral endplates along an insertion direction, the intervertebral implant comprising:
    an insertion end and an opposing engagement end spaced from the insertion end along the insertion direction when the implant is positioned between the first and second vertebral endplates;
    first and second opposed main surfaces configured to contact the respective first and second vertebral endplates, each of the first and second main surfaces defining an anterior end, and a posterior end, first and second main surfaces disposed between the insertion and engagement ends, each anterior end including a generally linear portion proximate the engagement end, each anterior end including a generally concave portion, and each posterior end including a generally linear portion proximate the engagement end, each posterior end including a generally convex portion, the generally linear portion of the anterior end converging with the generally linear portion of the posterior end at the engagement end for each of the first and second main surfaces;
    an anterior wall disposed between the first and second main surfaces, and the anterior wall disposed along the anterior ends of the first and second main surfaces;
    a posterior wall disposed between the first and second main surfaces, and the posterior wall disposed along the posterior ends of the first and second main surfaces, the anterior wall and the posterior wall converging at the insertion and engagement ends; and
    a slot defined at the engagement end, the slot continuously disposed between and at least partially along the anterior and posterior walls;
    a post positioned within the slot, the post spaced from at least one of the anterior or posterior walls, the post disposed at least partially between the first and second main surfaces, the post being elongate along a central post axis that extends through the first and second main surfaces and is perpendicular to the insertion direction, the post defining a length that extends along the central post axis the post defining a plurality of exposed facets configured such that the post is configured to be rotatably coupled to an insertion instrument, and a first facet of the plurality of facets is configured as a flat surface that extends along substantially an entirety of the length of the post.

6. The intervertebral implant of claim 5, wherein each anterior end is generally concave and each posterior end is generally convex.

7. The intervertebral implant of claim 6, wherein each of the first and second main surfaces includes a plurality of curved parallel ridges protruding from the respective surface and extending from the insertion end to the engagement end, each of the plurality of parallel ridges including a plurality of teeth.

8. The intervertebral implant of claim 5, wherein the anterior and posterior walls define a first height of the implant proximate the engagement end and a second height at the insertion end, the second height being less than the first height.

9. An intervertebral implant comprising:
    an insertion end and an opposing engagement end;

first and second opposed main surfaces configured to contact respective first and second vertebral endplates, each of the first and second main surfaces defining an anterior end, and a posterior end, each of the first and second main surfaces disposed between the insertion and engagement ends, each anterior end being generally concave, and each posterior end being generally convex;

an anterior wall disposed between the first and second main surfaces, the anterior wall disposed along the anterior ends of the first and second main surfaces;

a posterior wall disposed between the first and second main surfaces, the posterior wall disposed along the posterior ends of the first and second main surfaces, the anterior wall and the posterior wall converging at the insertion and engagement ends; and a slot defined at the engagement end, the slot continuously disposed between and at least partially along the anterior and posterior walls;

a post positioned within the slot, the post spaced from the anterior and posterior walls, the post disposed at least partially between the first and second main surfaces, the post defining a plurality of facets, the facets disposed around an entire periphery of the post, the facets configured such that the post is configured to be coupled to an insertion instrument;

a first abutment surface and a second abutment surface disposed within the slot, the first and second abutment surfaces spaced from the post, the first and second abutment surfaces being substantially linear, the first abutment surface being angularly offset from the second abutment surface, and the first and second abutment surfaces meet so as to define a non-zero angle, wherein the first abutment surface is configured to contact a first surface of the insertion instrument when the post is engaged with the insertion instrument so as to prevent further rotation of the intervertebral implant about the post in a first direction, and the second abutment surface configured to contact a second surface of the insertion instrument when the post is engaged with the insertion instrument so as to prevent further rotation of the intervertebral implant about the post in a second direction that is opposite the first direction.

10. The intervertebral implant of claim 9, wherein each of the first and second main surfaces includes a plurality of curved parallel ridges protruding from the respective surface and extending from the insertion end to the engagement end, each of the plurality of parallel ridges including a plurality of teeth.

11. The intervertebral implant of claim 9, wherein the anterior and posterior walls define a first height of the implant proximate the engagement end and a second height at the insertion end, the second height being less than the first height.

12. The intervertebral implant of claim 1, further comprising:

an axial bore defined between the anterior and posterior ends, and the axial bore disposed between the first and second main surfaces;

a plurality of markers, at least one of the markers disposed between the first and second main surfaces within one of the anterior or posterior walls, at least one other of the markers disposed generally transverse to the at least one of the markers, and the at least one other of the markers is elongate in a direction from the insertion end toward the axial bore.

13. The implant of claim 5 wherein the post is positioned within the slot so as to define a channel that extends between the anterior and posterior walls.

14. An intervertebral implant configured to be inserted into in an intervertebral space defined between a superior vertebra and an inferior vertebra, the intervertebral implant comprising:

an implant body that defines an insertion end, an opposed engagement end spaced from the insertion end along a longitudinal direction, a superior surface configured to face the superior vertebra, an inferior surface configured to face the inferior vertebra, the inferior surface being spaced from the superior surface in a transverse direction that is perpendicular to the longitudinal direction, the implant body further defining a first side surface, and a second side surface spaced from the first side surface along a lateral direction that is perpendicular to the transverse direction and the longitudinal direction, the first and second side surfaces extending between the superior and inferior surface, the implant body further defining a slot that extends from the first side surface to the second side surface, an abutment surface spaced from the engagement end, the abutment surface extending from the first side surface to the second side surface, and a post disposed within the slot and spaced from the abutment surface, the post being elongate along a central post axis that is aligned with the transverse direction and perpendicular to the lateral and longitudinal directions, the post defining a plurality of exposed facets spaced from the central post axis and extending along the transverse direction, the plurality of exposed facets being configured to engage complimentary facets of an insertion instrument, wherein the abutment surface is configured as a stop so as to prevent the insertion instrument from rotating about the central post axis.

15. The intervertebral implant of claim 14, wherein the abutment surface comprises a first portion and a second portion that is contiguous to the first portion, the first portion being angularly offset from the second portion so as to define a non-zero angle.

16. The intervertebral implant of claim 14, wherein the post defines a length that is aligned with the transverse directions, wherein a first facet of the plurality of exposed facets is configured as a flat surface that extends along substantially an entirety of the length of the post in the transverse direction.

17. The intervertebral implant of claim 14, further comprising a plurality of markers, at least one of the markers disposed between the first and second main surfaces within one of the anterior or posterior walls, at least one other of the markers disposed generally transverse to the at least one of the markers.

18. The intervertebral implant of claim 14, further comprising at least one lateral window disposed in at least one of the first side surface and second side surface.

* * * * *